United States Patent [19]

Warriner

[11] Patent Number: Plant 6,282

[45] Date of Patent: Sep. 13, 1988

[54] ROSE PLANT JACTRO

[75] Inventor: William A. Warriner, Tustin, Calif.

[73] Assignee: Jackson & Perkins Company, Medford, Oreg.

[21] Appl. No.: 892,546

[22] Filed: Aug. 4, 1986

[51] Int. Cl.[4] ..... A01H 5/00

[52] U.S. Cl. ..... Plt./11

[58] Field of Search ..... Plt./11

*Primary Examiner*—James R. Feyrer

*Attorney, Agent, or Firm*—Majestic, Gallagher, Parsons & Siebert

[57] ABSTRACT

A hybrid tea rose variety having high centered delicately colored flowers borne on upright vigorous plants. Flowers have a pleasant fragrance, are stiff petalled and are carried on thorny, glandular peduncles. Leaves are an attractive glossy green.

1 Drawing Sheet

This present invention relates to a new and distinct variety of rose plant of the hybrid tea class which was originated by crossing the variety White Masterpiece, U.S. Plant Pat. No. 2,998, with the variety Grand Masterpiece, U.S. Plant Pat. No. 4,767.

The primary objective of this breeding was to produce a new rose variety of the hybrid tea class with exhibition quality flowers and a vigorous upright plant. This objective was substantially achieved along with other desirable improvements as evidenced by the following unique combination of characteristics which are outstanding in the new variety and which distinguish it from its parents as well as from all other varieties of which I am aware:

1. Tall, vigorous plant;
2. Large, high centered flowers, blending white with a delicate pink;
3. Pleasant fragrance;
4. Stiff petals;
5. Stiff, thorny glandular penduncles; and
6. Glossy, dark green foliage.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—White Masterpiece, U.S. Plant Pat. No. 2,998.

*Pollen parent.*—Grand Masterpiece, U.S. Plant Pat. No. 4,767.

Classification:

*Botanical.*—Rosa hybrid.

*Commercial.*—Hybrid tea.

FLOWER

Observations made from specimens grown in a greenhouse at Irvine, Calif. in Spring, 1986.

Blooming habit: Continuous.

Bud:

*Size.*—1½"-2" when petals start to unfurl.

*Form.*—Pointed ovoid.

*Color.*—When sepals first divide, Creamy White (White Group 155A) with Pink edges (Red Group 56A to B); when half blown, upper side of petals White edged in Pink with Pink center. White Group 155A with Red Group 56A to B; lower side of petals White (White Group 155A) edged in Pink (Red Group 56A).

*Sepals.*—Color: Green Group 138B. Three appendaged sepals lightly appendaged. Two appendaged sepals hairy edge.

*Receptacle.*—Color: medium green. Shape: funnel. Size: medium. Surface: smooth.

*Peduncle.*—Length: medium. Surface: prickly and glandular. Color: medium green. Strength: stiff, erect.

Open bloom:

*Size.*—Large. Average open size 4"-5".

*Borne.*—Singly.

*Stems.*—Long to medium, strong.

*Form.*—When first open, high center. Permanence: outer petals curl back.

*Petalage.*—Number of petals under normal conditions: 35.

*Color.*—Center of flower upper side of petals, overall impression of delicate Pink edges closely resembling Red Group 56A to C with the rest of the petal Creamy White (White Group 155A); reverse side of petals, similar to upper side with slightly more White showing. Base of petals, a small Yellow area, Yellow Group 5C. Major color: Pink (Red Group 56A to B), White (White Group 155A).

*Variegations.*—None.

*Discoloration.*—General tonality at end of first day: none. Third day: becoming more Pink and less White.

*Fragrance.*—Moderate to strong.

Petals:

*Texture.*—Thick.

*Shape.*—Round.
*Form.*—Tips slightly recurved.
*Arrangement.*—Imbricated. Petaloids in center, few.
*Persistence.*—Drop off cleanly.
*Lastingness.*—On the plant, long. As cut flower, long.

Reproductive parts:
*Anthers.*—Medium. Color: Reddish brown. Arrangement: Regular around styles.
*Filaments.*—Color: Reddish brown.
*Pollen.*—Lemon yellow.
*Styles.*—Color: reddish.
*Stigmas.*—Color: greenish white.

PLANT

Form: Bush.
Growth: Vigorous, upright.
Foliage:
*Number of leaflets on normal mid-stem leaves.*—5 to occasionally 7.
*Size.*—Large to medium.
*Quantity.*—Normal.
*Color.*—New foliage: reddish. Old foliage: glossy green.

Leaflets:
*Shape.*—Oval pointed.
*Texture.*—Glossy, smooth.

*Edge.*—Serrated.
*Serration.*—Single, small.
*Petiole.*—Rachis: Color: reddish. Underside: rough, with prickles.
*Stipules.*—Long and narrow, serrated.
*Disease resistance.*—Susceptible to mildew, under normal growing conditions at Irvine, Calif.

Wood:
*New wood.*—Color: reddish. Bark: smooth.
*Old wood.*—Color: green. Bark: smooth.

Prickles:
*Quantity.*—On main canes from base: ordinary. On laterals from main canes: ordinary.
*Form.*—Medium, hooked downward.
*Color when young.*—Red.

Small prickles:
*Quantity.*—On main stalks, none. On laterals, none.

I claim:

1. A new and distinct variety of rose plant of the hybrid tea class, substantially as herein shown and described, characterized particularly as to novelty by the unique combination of high centered delicately colored flowers borne on upright vigorous plants. Flowers have a pleasant fragrance, are stiff petalled and are carried on thorny, glandular peduncles. Leaves are an attractive glossy green.

* * * * *

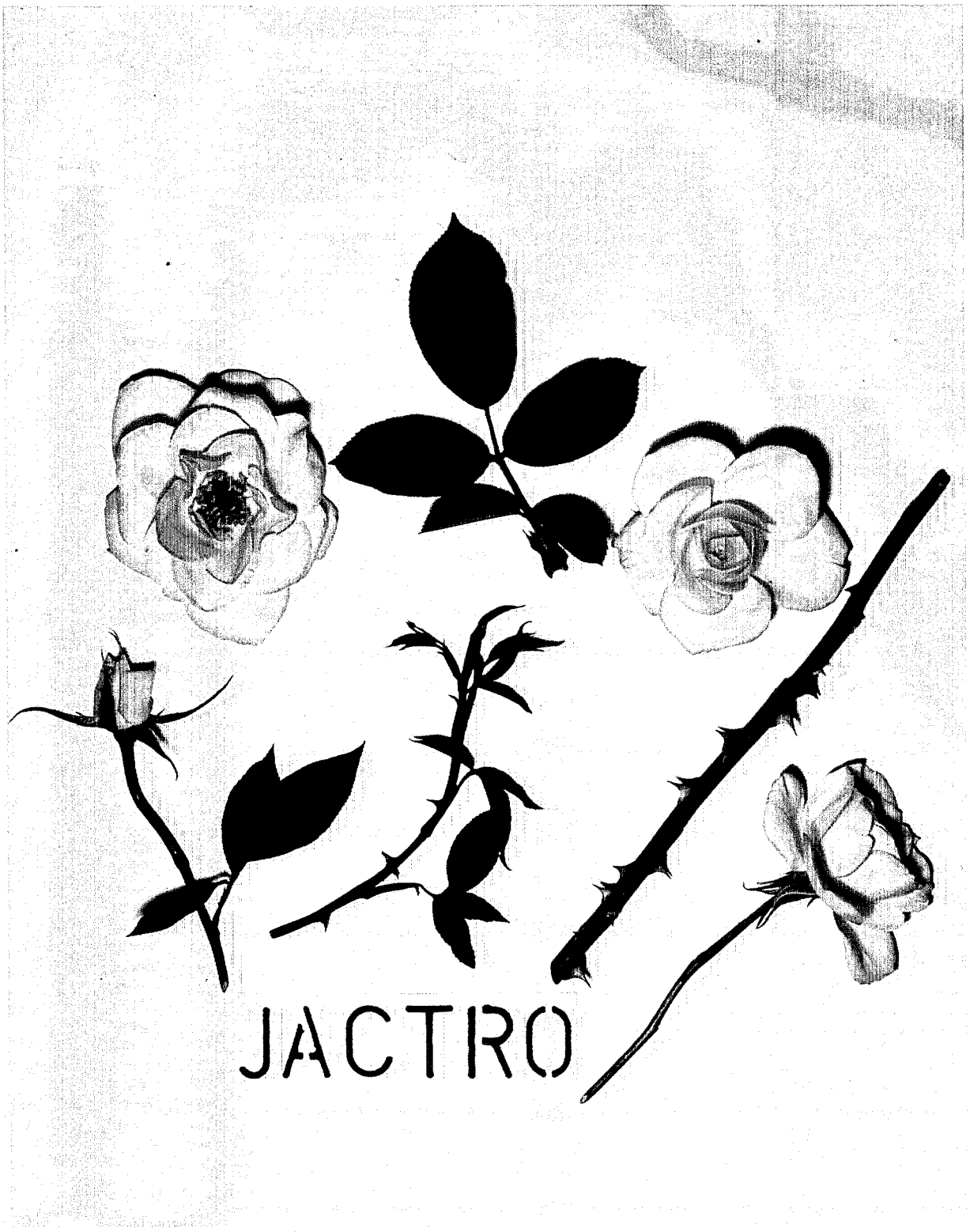
JACTRO